(12) United States Patent
Talebpour et al.

(10) Patent No.: US 7,723,127 B2
(45) Date of Patent: May 25, 2010

(54) IMMUNOASSAY WITH EXTENDED DYNAMIC RANGE

(75) Inventors: Samad Talebpour, Richmond Hill (CA); Stephen W. Leonard, Unionville (CA)

(73) Assignee: Novx Systems Inc., Markham, ON (CA)

( * ) Notice: Subject to any disclaimer, the term of this patent is extended or adjusted under 35 U.S.C. 154(b) by 1032 days.

(21) Appl. No.: 11/070,282

(22) Filed: Mar. 3, 2005

(65) Prior Publication Data

US 2006/0199236 A1     Sep. 7, 2006

(51) Int. Cl.
*G01N 33/542* (2006.01)
*G01N 33/557* (2006.01)
*G01N 33/53* (2006.01)
*G01N 33/00* (2006.01)

(52) U.S. Cl. .................. 436/537; 436/517; 435/7.9; 435/7.93

(58) Field of Classification Search .............. None
See application file for complete search history.

(56) References Cited

U.S. PATENT DOCUMENTS

| | | | |
|---|---|---|---|
| 4,600,690 A | * | 7/1986 | Karmen et al. ............... 435/7.9 |
| 5,585,241 A | | 12/1996 | Lindmo |
| 5,672,475 A | * | 9/1997 | Lee et al. ............... 435/6 |
| 5,919,642 A | | 7/1999 | Khanna et al. ............... 435/7.9 |
| 6,551,788 B1 | | 4/2003 | Bell | 
| 2004/0253657 A1 | | 12/2004 | Ullman et al. ............... 435/7.92 |

FOREIGN PATENT DOCUMENTS

WO     89/11101     11/1989

* cited by examiner

*Primary Examiner*—Mark L Shibuya
*Assistant Examiner*—Christine Foster
(74) *Attorney, Agent, or Firm*—Hill & Schumacher; Lynn C. Schumacher

(57) ABSTRACT

The present invention provides a method of performing a competitive assay for the detection and quantification of an analyte over an extended dynamic range. This is achieved by a multi-step sample addition method whereby different concentrations of sample are added at different times during the assay that produces a dose-response curve with multiple windows of detection. This multi-step sample addition method causes the dose-response curve of the composite assay to broaden, dramatically increasing the assay dynamic range.

37 Claims, 13 Drawing Sheets

IMMUNOASSAY WITH EXTENDED DYNAMIC RANGE

FIELD OF THE INVENTION

The present invention is related to immunoassays with extended dynamic range.

BACKGROUND OF THE INVENTION

Affinity-based immunoassays, due to their sensitivity, are routinely used to detect and measure the presence and the concentration of an analyte in a sample. The analyte may be any of the wide variety of materials, such as drugs, pollutants, chemicals, contaminants, or the like. The most common approach for performing detection and quantification of analytes with low molecular mass (<1000) is the competitive immunoassay. This assay, which exists in multiple formats, involves a target analyte, a specific receptor that binds to the analyte, and a corresponding analyte-conjugate, which consists of a target analyte (or a derivative of the target analyte) conjugated to a detectable label such as an enzyme.

Competitive assays are known to exhibit a nonlinear dose-response curve, the shape of which is dictated by the mass-action principle and the affinity of the receptor for the analyte and analyte-conjugate. The dynamic range offered by such assays is often limited to approximately one order of magnitude when using monoclonal antibodies as receptors. Unfortunately, the clinically relevant range of concentrations of a large number of important analytes can be much larger than an order of magnitude, thereby exceeding the measurable range of most competitive assays.

The most straightforward technique to extend the dynamic range of an assay is to dilute the sample and rerun the assay. This method preserves the accuracy of the assay and increases the dynamic range. Such a strategy might be reasonable for clinical settings that perform screening, in which analyte concentrations are usually distributed over a very limited range of concentrations. In such cases, the probability of needing dilution is very low and therefore infrequent. Clinics that perform high-throughput screening are particularly suited towards dilution as a means of extending the assay dynamic range since the time and cost associated with sample dilution is relatively inconsequential.

However, there are many other non-screening clinical settings in which samples can exist with a very broad distribution of analyte concentrations, making it necessary to dilute samples frequently. For example, methadone maintenance clinics (that monitor the compliance of drug addicts under therapy for their addiction) require the frequent and accurate testing of a population of patients with wide range of drug concentrations. If dilution is used to provide the needed assay dynamic range, considerable cost can result; both in terms of the cost of additional reagents and also as a result of the longer time interval before a result is obtained. Smaller clinics are particularly sensitive to the increased cost associated with dilution since they cannot benefit from the same economies of scale that the high throughput clinics enjoy.

U.S. Pat. No. 5,585,241 and WO8911101 describe assay techniques that utilize high and low affinity receptors, respectively, coated onto different types of monodisperse particles. However, these methods require the production of two different types of receptors for the analyte, a task that requires long development times. Furthermore, it is difficult to satisfy the requirement for highly controlled receptor affinity over multiple batches of reagents. U.S. Pat. No. 6,551,788 provides assays having a wide dynamic range by simultaneously incubating a sample with two or more independently determinable classes of a receptor coated particles differing from each other in size. Again, this method requires the costly and onerous task of preparing dedicated reagents with a high degree of control.

What is therefore needed is an assay method that offers an extended dynamic range in a simple, cost-effective and practical method without requiring a separate assay and the consumption of additional reagents.

SUMMARY OF THE INVENTION

Accordingly, a method for conducting a novel composite assay is provided in which a multi-step sample addition process is employed, whereby different concentrations of sample are added at different times during the assay. The multi-step sample addition method causes the dose-response curve of the composite assay to broaden, dramatically increasing the assay dynamic range.

The inventive assay is conducted as follows. An initial sample volume that is being assayed for the target analyte, and a reagent containing analyte conjugated to a label, are dispensed into a vessel. A second reagent containing receptors with a high affinity for the analyte is then dispensed into the same vessel, at which point the reaction begins. The mixture is then incubated for an initial time period. A second sample volume, containing more sample than the initial sample, is then dispensed into the vessel. The volume and concentration of the second sample is chosen to give a preferred dilution factor of the first sample addition step relative to the second sample addition step. The new mixture is then incubated for a second time interval, after which a signal related to the amount of bound or unbound analyte is measured. A pre-established dose-response curve is then used to infer the analyte concentration from the measured signal. The dose-response curve of the composite assay can be optimized by controlling the sample dilution factor and the two incubation times.

Thus, the present invention provides a method of performing an assay for a target analyte in a sample which may contain a concentration of target analyte, comprising the steps of:
a) combining in a vessel a first volume containing a first quantity of said sample and a first quantity of dilution buffer, a first reagent volume containing a known concentration of the target analyte conjugated to an enzyme, and a second reagent volume containing one or more substrates upon which said enzyme acts and receptors having affinity for the target analyte;
b) thermally incubating said vessel for a first time interval;
c) adding a second volume containing a second quantity of said sample and a second quantity of dilution buffer to said vessel, whereby a ratio of an amount of said sample in said second volume to the amount of said sample in said first volume is equal to a prescribed dilution factor;
d) thermally incubating said vessel for a second time interval, during which time an assay signal generated by the action of said enzyme on said one or more substrates is measured; and
e) relating said measured assay signal to a concentration of said target analyte in said sample using a pre-determined dose-response curve.

In another aspect of the invention, the composite assay method can be modified to obtain high sensitivity over a broad detection window. This is accomplished by the following method, in which the dilution factor is varied on a per-assay basis in order to give a measurement with optimal accuracy. A fixed volume of diluted sample is initially added to a reaction vessel. After the first incubation period, the signal is measured and used to obtain an estimate of the analyte concentration via a pre-determined dose-response curve. The optimal dilution factor of the first sample relative to the second sample is then calculated from the ratio of the analyte concentration at which the dose-response curve has the maximum slope to the estimated analyte concentration. A second sample with a volume and concentration in agreement with the calculated dilution factor is then added to the vessel. After incubating for a second time period, the signal is again measured. The analyte concentration is then accurately inferred from a pre-established dose-response curve for the composite assay at the appropriate dilution factor.

Thus, in another aspect of the invention there is provided a method of performing an assay for a target analyte in a sample which may contain a concentration of a target analyte, comprising the steps of:
a) combining in a vessel a first volume containing a first quantity of said sample and a first quantity of dilution buffer, and a first reagent volume containing a known concentration of the target analyte conjugated to an enzyme, and a second reagent volume containing one or more substrates upon which said enzyme acts and receptors having affinity for the target analyte;
b) thermally incubating said vessel for a first time interval, during which time a first assay signal generated by the action of said enzyme on said one more substrates is measured;
c) estimating said concentration of the target analyte in said sample by relating said measured first assay signal to said concentration of said target analyte in said sample using a pre-determined dose-response curve corresponding to said first assay signal;
d) calculating an optimal dilution factor by dividing a concentration at which said pre-determined dose-response curve has a maximal slope by said estimated concentration of said target analyte in said sample;
e) adding a second volume containing a second quantity of said sample and a second quantity of dilution buffer to said vessel, whereby a ratio of an amount of said sample in said second volume to the amount of said sample in said first volume is equal to said optimal dilution factor;
f) thermally incubating said vessel for a second time interval, during which time a second assay signal generated by the presence of said enzyme conjugated to said target analyte is measured; and
g) relating said measured second assay signal to said concentration of said target analyte in said sample using a dose-response curve corresponding to said second assay signal.

In another aspect of the invention there is provided a method of performing an assay for a target analyte in a sample which may contain a concentration of a target analyte, comprising the steps of:
a) performing a first sample addition step including combining in a vessel a first volume containing a first quantity of said sample and a first quantity of dilution buffer, and a first reagent containing a known concentration of the target analyte conjugated to an enzyme, and a second reagent volume containing one or more substrates upon which said enzyme acts and receptors having affinity for the target analyte;
b) thermally incubating said vessel for a first time interval;
c) performing one or more additional sample addition and incubation steps including adding an additional volume containing an additional quantity of said sample and an additional quantity of dilution buffer to said vessel, whereby the ratio of an amount of said sample in said additional volume to the amount of said sample used in an immediately preceding sample addition step is equal to a prescribed dilution factor and thermally, incubating said vessel for an additional time interval;
d) performing a final sample addition step including adding a final volume containing a final quantity of said sample and a final quantity of dilution buffer to said vessel, whereby the ratio of an amount of said sample in said final volume to the amount of said sample used in an immediately preceding sample addition step is equal to a prescribed dilution factor;
e) thermally incubating said vessel for a final time interval, during which time an assay signal generated by the action of said enzyme on said one more substrates is measured; and
f) relating said measured assay signal to a concentration of said target analyte in said sample using a pre-determined dose-response curve.

In another aspect of the invention there is provided a method of performing an assay for a target analyte in a sample which may contain a concentration of a target analyte, comprising the steps of:
a) combining in a vessel a first volume containing a first quantity of said sample and a first quantity of dilution buffer, a first reagent volume containing a known concentration of the target analyte conjugated to a label, and a second reagent comprising receptors having affinity for the target analyte, where said receptors are immobilized to a solid phase;
b) thermally incubating said vessel for a first time interval;
c) adding a second volume containing a second quantity of said sample and a second quantity of dilution buffer to said vessel, whereby a ratio of an amount of said sample in said second volume to the amount of said sample in said first volume is equal to a prescribed dilution factor;
d) thermally incubating said vessel for a second time interval;
e) separating a supernatant from said solid phase and measuring a signal generated by the presence of said label conjugated to said target analyte; and
f) relating said measured signal to a concentration of said target analyte in said sample using a pre-determined dose-response curve.

In a final aspect of the invention, a method of modifying a conventional assay to obtain a broadened detection window is disclosed. This method applies to any assay that exhibits an S-shaped dose-response curve, regardless of the assay technology. The improved assay method is performed by adding a quantity of pure analyte to either an assay reagent or the sample and subsequently performing the assay using the known conventional protocol. The addition of pure analyte broadens the dose-response curve of the assay, decreasing the maximum assay accuracy but increasing the detection window.

Thus, in another aspect of the invention there is a method of performing an assay for a target analyte, where said assay is characterized by an S-shaped dose-response curve, resulting in a broadened detection window, comprising the steps of:
a) adding a known quantity of said target analyte to either a sample that may contain a concentration of said target analyte or a reagent used in said assay; and
b) performing said assay on said sample, wherein said step a) results in a broadened detection window, with improved performance at low target analyte concentrations.

A further understanding of the functional and advantageous aspects of the invention can be realized by reference to the following detailed description and drawings.

BRIEF DESCRIPTION OF THE DRAWINGS

The invention will be more fully understood from the following detailed description thereof taken in connection with the accompanying drawings, which form a part of this application, and in which.

DETAILED DESCRIPTION OF THE INVENTION

This invention relates to a method of assaying one analyte in a sample. More specifically, it provides an improved competitive assay that is capable of providing an enhanced dynamic range, with multiple windows of detection.

The term "receptor", as used herein, means antibodies, DNA, RNA, aptamers, molecularly imprinted polymers, or any other species capable of exhibiting a specific binding affinity for the analyte.

The term "analyte" or "target analyte", as used herein, means any species whose presence or concentration in a sample is sought.

The term "detection window", as used herein, means a continuous range of analyte concentrations over which the coefficient of variation (CV) is below a desired value.

The term "dynamic range", as used herein, means the ratio of the largest analyte concentration within the detection window to the smallest analyte concentration in the detection window.

Competitive assays of the prior art are performed by incubating a volume of sample (that may contain a target analyte) with a known quantity analyte-conjugate in the presence of a known quantity of receptors that are specific to the analyte and the analyte-conjugate. The analyte in the sample and the analyte-conjugate compete for binding sites of the receptors, which may either reside in a homogeneous format or bound to a solid phase in a heterogeneous format. Following an incubation time interval, a signal related to the number of bound or unbound analyte-conjugates is measured. This is achieved using one of many formats known in the prior art, such as the competitive homogenous enzyme immunoassay (EIA). In the competitive homogeneous EIA format, enzyme conjugated to the analyte acts on a chromogenic substrate, producing colour that is measured as optical absorbance. The binding of the analyte-conjugate to a receptor decreases the activity of the enzyme, producing less optical absorbance. The measured absorbance is therefore related to the analyte concentration using a predetermined dose-response curve. Such competitive assays typically exhibit a dynamic range of less than an order of magnitude.

The present invention improves upon conventional competitive assays by dramatically increasing the assay dynamic range. This is achieved using a novel composite assay involving a multi-step sample addition process, in which precise sample volumes are added to a reaction vessel during the process of assay incubation. Such an intra-assay sample addition scheme has been observed to produce the advantageous result of broadening the dynamic range of a competitive assay.

Figure 1:
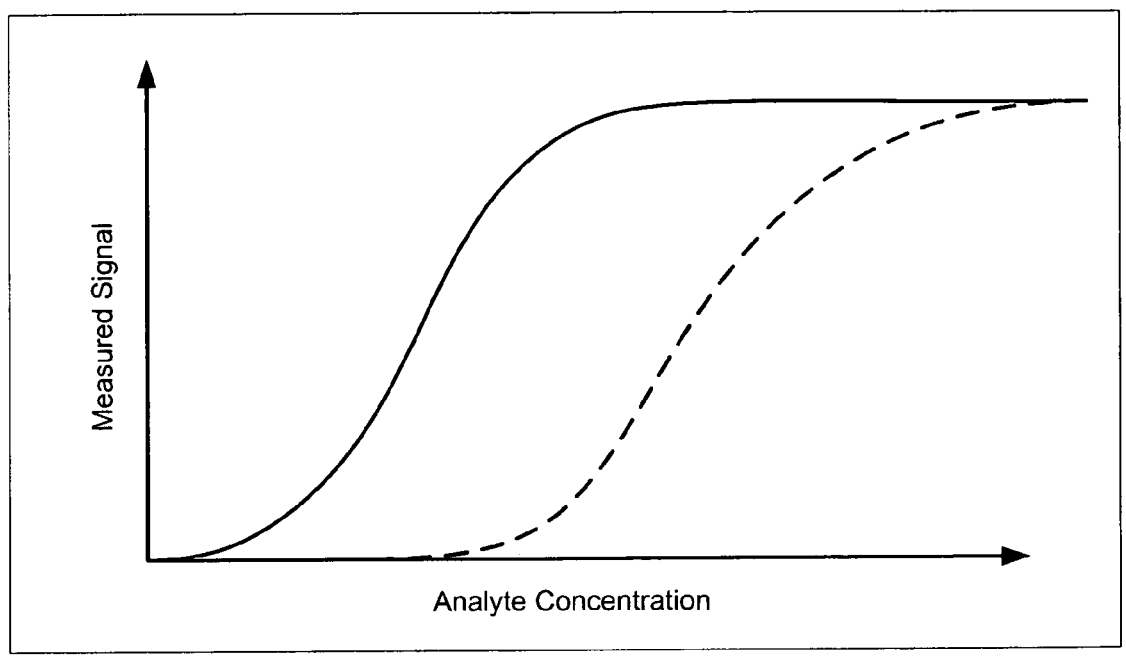
FIG. 1 is an illustration of a typical set of dose-response curves for a prior art competitive assay.

The novel composite assay disclosed herein can be broadly understood by contrasting the prior art and the inventive methods of performing a competitive assay. The dose response of a prior-art competitive assay, in which the measured signal is linearly related to the number of unbound analyte-conjugates, is illustrated in FIG. 1. In the case of an undiluted sample, the solid logistic curve is obtained. If the sample is diluted, then the dose-response curve shifts to higher sample concentrations, as indicated by the dashed logistic curve.

The dose-response curve of the competitive assay is now considered in the case of a composite assay in which diluted and undiluted samples are both added during the assay. After a diluted sample is initially added and incubated with the analyte-conjugate, the reaction progresses towards generating the dashed dose-response curve of FIG. 1. After an incubation period, the undiluted sample is added and the new mixture is incubated. The reaction then shifts towards producing the solid dose-response curve of FIG. 1. If sufficient time is provided to achieve chemical equilibrium, then the final dose-response curve will be, in theory, almost exactly that of the solid curve in FIG. 1 (shifted slightly due to the presence of the small amount of analyte in the diluted sample) since the amount of analyte present in the reaction vessel is almost equal to that of the undiluted sample.

If, however, chemical equilibrium is not achieved after the addition of the undiluted sample, then the measured dose response curve will not lie on either curves of FIG. 1. Instead, it can be appreciated that the final number of analyte-conjugates will be between the value obtained with the single competitive diluted and undiluted samples. In other words, the dose-response curve will lie between the solid and dashed curves of FIG. 1. Such an intermediate, non-equilibrium, dose-response curve is shown as the thick solid curve in FIG. 2. This intermediate curve, obtained by performing the inventive composite assay, spans a much wider dynamic range than the comparative prior art assay. The exact form of the composite assay curve depends on the relative amounts of sample added in the two steps and the timing of the incubation.

Figure 3:
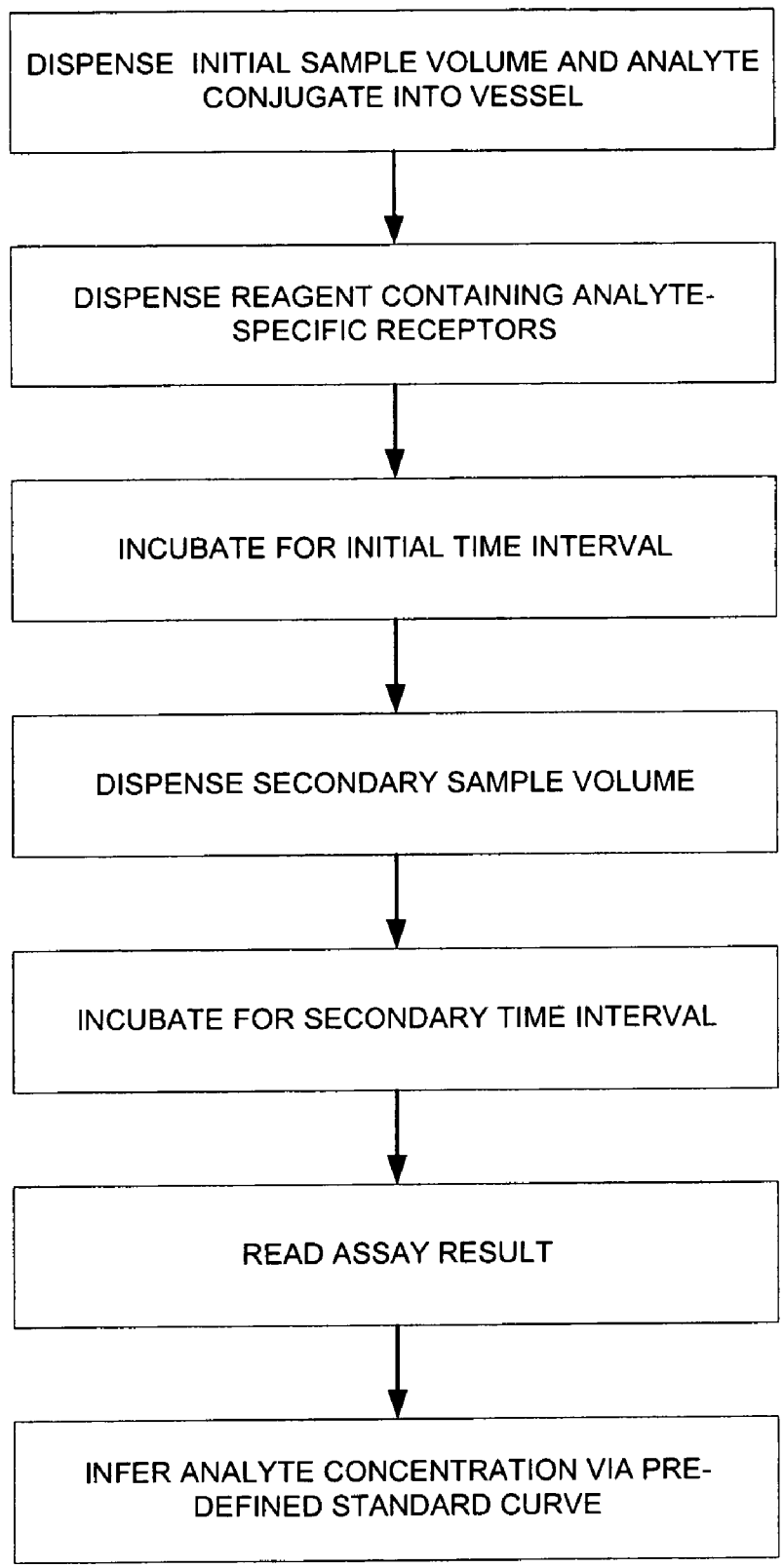
FIG. 3 illustrates a method for carrying out the composite assay in the case of a homogeneous competitive assay.

The assay method described above is schematically shown in the flow chart of FIG. 3 for the case of a homogeneous competitive assay. In the first step, an initial sample volume that is being assayed for the target analyte, and a reagent containing the analyte-conjugate, are dispensed into a vessel. A second reagent containing the analyte-specific receptors is then dispensed into the same vessel, at which point the reaction begins. Alternatively, for the case of a heterogeneous assay with a single solid phase, the sample volume and the analyte-conjugate are dispensed into a second vessel containing the receptors bound to a solid phase. The mixture is then incubated for an initial time period. A second sample volume, with a larger sample volume than the initial sample, is then dispensed into the vessel. The new mixture is then incubated for a second time interval, after which the assay is completed.

After the completion of the assay, the result is read using an appropriate detection scheme. For example, in a homogeneous assay in which enzymes that act upon a chromogenic substrate are conjugated to the analyte, optical absorbance is performed. In a preferred embodiment of the invention, the detection method provides a measure of the total number of bound or unbound analyte-conjugates. In the aforementioned case of an enzyme conjugated to an analyte, this is achieved by measuring the rate of change of absorbance rather than the net absorbance signal. In another example, if a fluorometric label is employed, the direct fluorescence signal is used as a measure of the total number of bound or unbound analyte-conjugates.

The assay method can be further explained by consideration of a non-limiting example, in which a homogeneous competitive assay is conducted for the quantification of EDDP in urine. EDDP is a metabolite of methadone, a replacement drug that is commonly administered to drug abusers who are under therapeutic treatment for drug addiction. A commercial enzyme immunoassay (EIA) is employed to demonstrate the performance of the prior art method. In this assay, the analyte-conjugate is enzyme-labeled EDDP, and this conjugate competes with EDDP in the sample (the analyte) for a limited number of antibody binding sites. As the amount of analyte in the sample increases, the amount of the analyte-conjugate bound to the antibodies decreases, resulting in increased enzyme activity, since the binding of enzyme-analyte-conjugate to an antibody inhibits the enzyme activity. The rate of change of substrate production, which is linearly related to the number of bound (or unbound) enzyme conjugates, is measured via optical absorbance at a wavelength of 340 nm.

The commercial EIA has two reagents, henceforth referred to as $R_1$ and $R_2$. Reagent $R_1$ contains the receptors, which includes monoclonal antibodies against EDDP and the substrates, which include glucose-6-phosphate (G6P) and nicotinamide adenine dinucleotide (NAD). The second reagent, $R_2$, contains the analyte-conjugate, which is EDDP labeled with the enzyme glucose-6-phosphate dehydrogenase (G6PDH). A change in optical absorbance is produced by the action of the enzyme G6PDH on the substrates G6P and NAD, which changes NAD to NADH.

The EIA reagents described above were used to illustrate the underlying principle of the invention, whereby the composite assay method produces a dose-response curve that lies between the dose-response curves of two assays performed with the diluted and undiluted samples individually. In this experiment, the competitive homogeneous assay was performed in three wells of a 96-well microplate format. In the first well, 20 μL of sample containing 1000 ng/ml of EDDP was mixed with 30 μL of $R_2$. Subsequently, 80 μL of $R_1$ was added to this well. In the second and third wells, only 2 μL of sample containing 1000 ng/ml of EDDP was mixed with 30 μL of $R_2$. 80 μL of $R_1$ was also subsequently added to the second and third wells. The microplate was then vortexed for 30 seconds and the absorbance of each well was measured at a wavelength of 340 nm for 5 minutes, with a measurement interval of 30 seconds. During the optical measurements, the microplate was maintained at room temperature. After the 5 minutes of optical measurements and an additional incubation interval of 2 minutes, 18 μL of sample containing 1000 ng/ml (of EDDP) was added to the third well. The microplate was then vortexed and the absorbance of each well was then read for 30 minutes, again with a measurement interval of 30 seconds.

Figure 4:
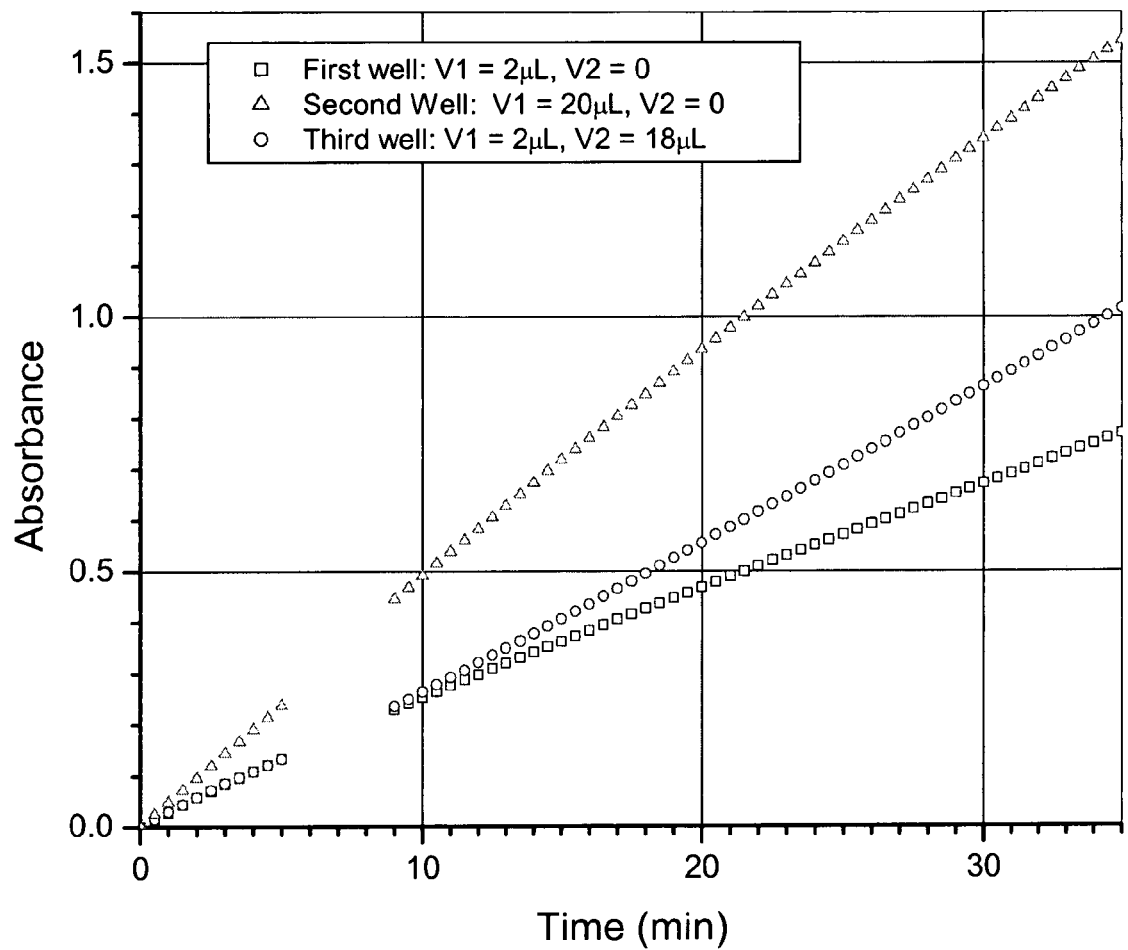
FIG. 4 is a set of curves presenting the absorbance as a function of incubation time for a homogeneous competitive assay for EDDP (a metabolite of methadone), which is performed in conventional and composite manners. The concentration of EDDP in the sample is 1000 ng/ml.

It can therefore be understood that the first well in the above experiment represents the prior art assay conducted with an undiluted sample and the second well represents the prior art assay conducted with a diluted sample. However, the third well, to which 2 μL of sample was first added, and then 18 μL was later added, represents the inventive composite assay method. The results are presented in FIG. 4, where the measured absorbance is plotted as a function of time, with the initial absorbance values subtracted from the data. From this figure, the rates of change of absorbance (at a time of 30 minutes) were calculated to be 20.2, 39.5, and 31.1 mAU/min for the first, second and third wells, respectively. The curves in FIG. 4 and the measured rates of change of absorbance show that both the absorbance and rate of change of absorbance of the inventive assay fall between the values obtained for the prior art diluted and undiluted assays. This result clearly confirms the novel aspect of the invention, whereby an intermediate dose-response curve can be obtained via the prescribed method.

This result can be further investigated by comparing the complete dose-response curve of the prior art undiluted assay to that of the inventive assay for EDDP, in which several different analyte concentrations are used to accurately fit a mathematical function. The prior art competitive assay for EDDP was first conducted in a 96-well microplate format. In each of eight wells within a microplate, 20 μL of sample containing a known concentration of EDDP was mixed with 30 μL of $R_2$. The concentrations of the eight EDDP samples added to the microplate wells were 0, 75, 150, 300, 500, 1000, 2300 and 9000 ng/ml. Subsequently, 80 μL of $R_1$ was added to each microplate well. The microplate was then vortexed for 30 seconds before measuring the absorbance at 340 nm at intervals of 30 seconds over 35 minutes. During the absorbance measurements, the microplate was kept at room temperature.

Figure 5:
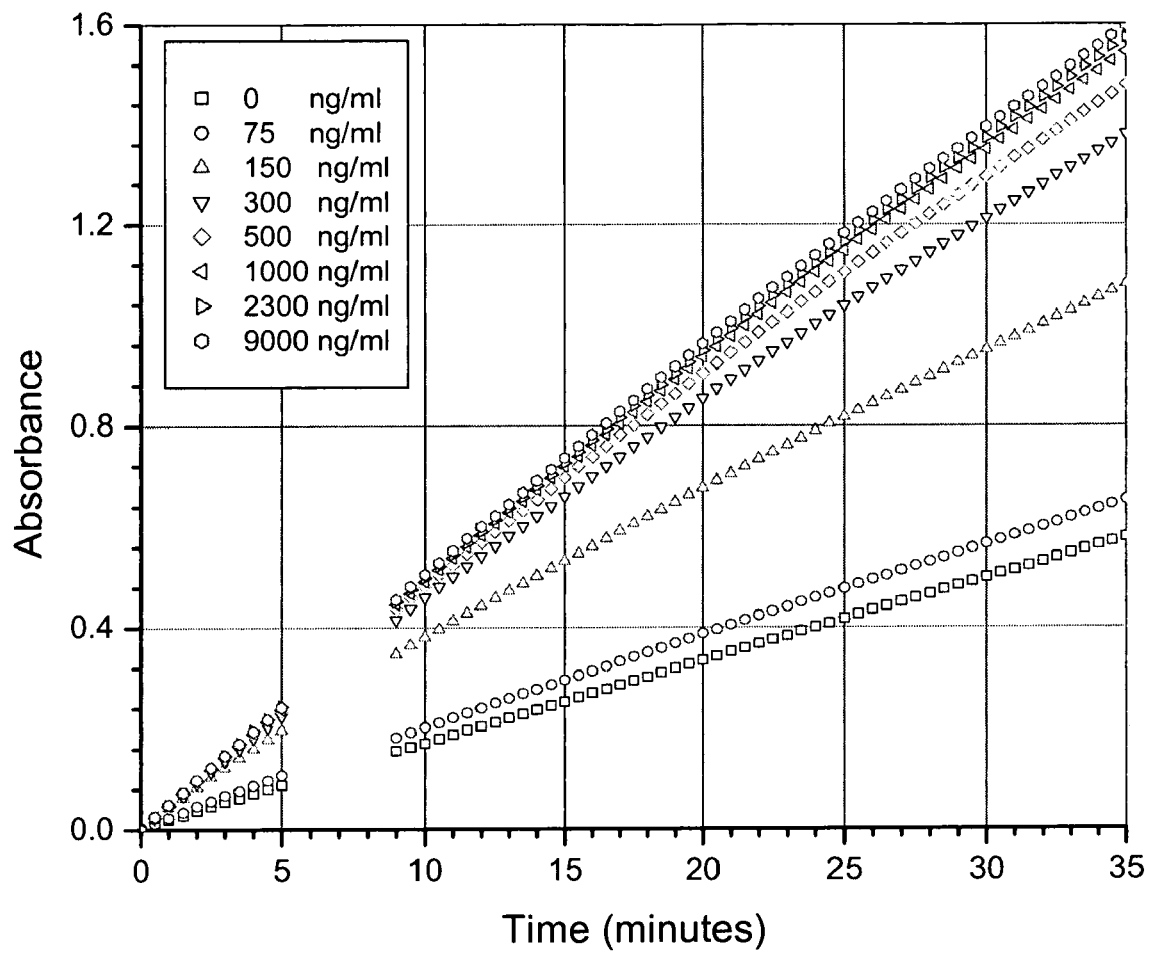
FIG. 5 is a set of curves describing the absorbance as a function of incubation time for a prior art competitive assay where the analyte is EDDP.
Figure 6:
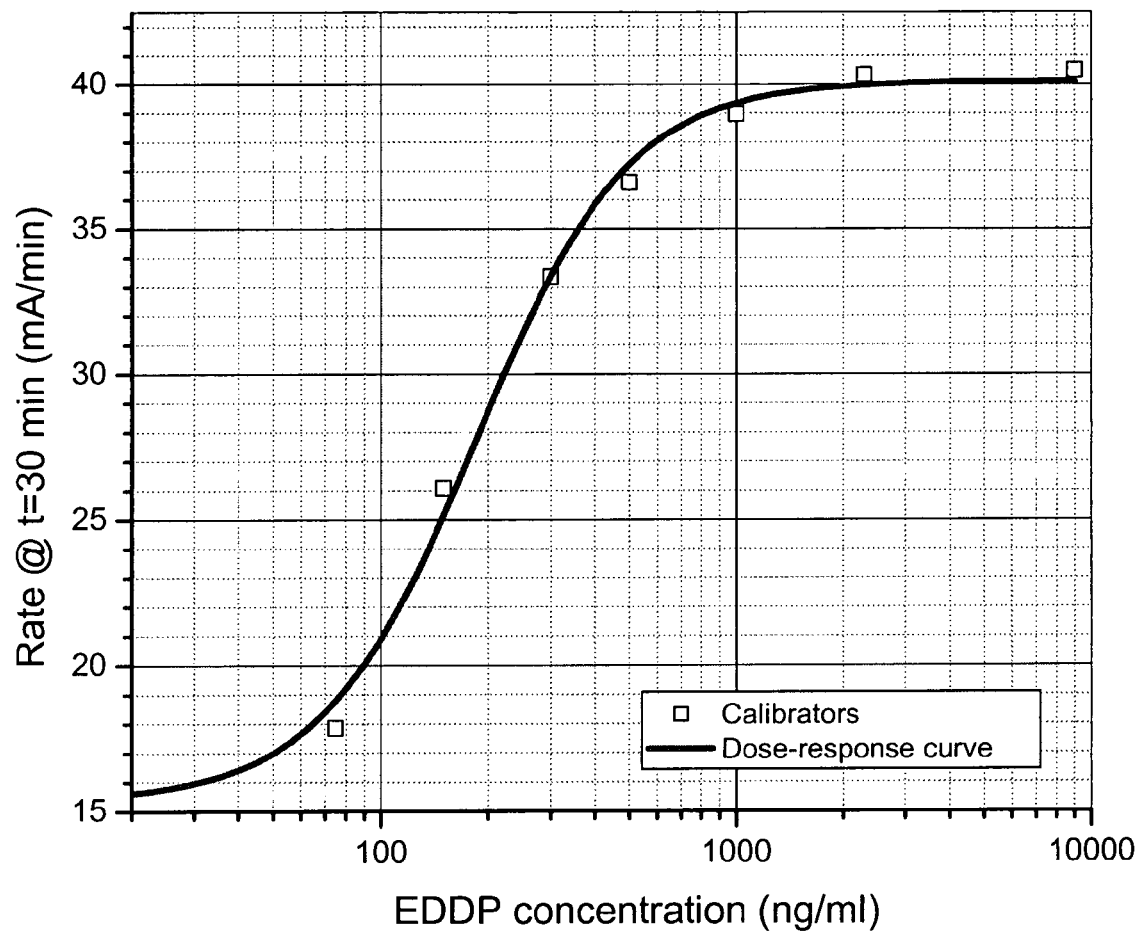
FIG. 6 shows the rate of change of absorbance after 30 minutes of incubation for the curves in FIG. 4. A logistic curve, which is fitted to measured data, represents the dose-response curve.

The measured absorbance values for the eight samples are plotted in FIG. 5. The initial absorbance values have been subtracted from the data in order to remove any sample-dependent background absorbance. The assay result is inferred from the rate of change of absorbance, which is plotted in FIG. 6 at a time of 30 minutes from the commencement of the assay. As shown in the figure, the measured rates of absorbance change are accurately fit by a logistic function, producing a smooth dose-response curve for the prior art assay. The detection window of the assay, defined in this case by the range of analyte concentrations that fall between 10% and 90% of the maximum signal (after subtracting the fixed offset), is approximately 58-580 ng/ml and the dynamic range is approximately 10.

The inventive composite assay was then conducted using a separate microplate. In each of eight wells within the microplate, 2 µL of sample containing a known concentration of EDDP was mixed with 30 µL of $R_2$. The concentrations of the eight EDDP samples added to the microplate wells were the same as in the prior art competitive assay described above.

Subsequently, 80 µL of $R_1$ was added to each microplate well. The microplate was then vortexed for 30 seconds and the absorbance was read for 5 minutes at intervals of 30 seconds, keeping the microplate at room temperature. A sample volume of 18 µL was then added (each well receiving the same sample concentration as in the initial 2 µL sample volume) before again vortexing the microplate. The absorbance was then read at intervals of 30 seconds over 30 minutes, again keeping the microplate at room temperature.

Figure 7:
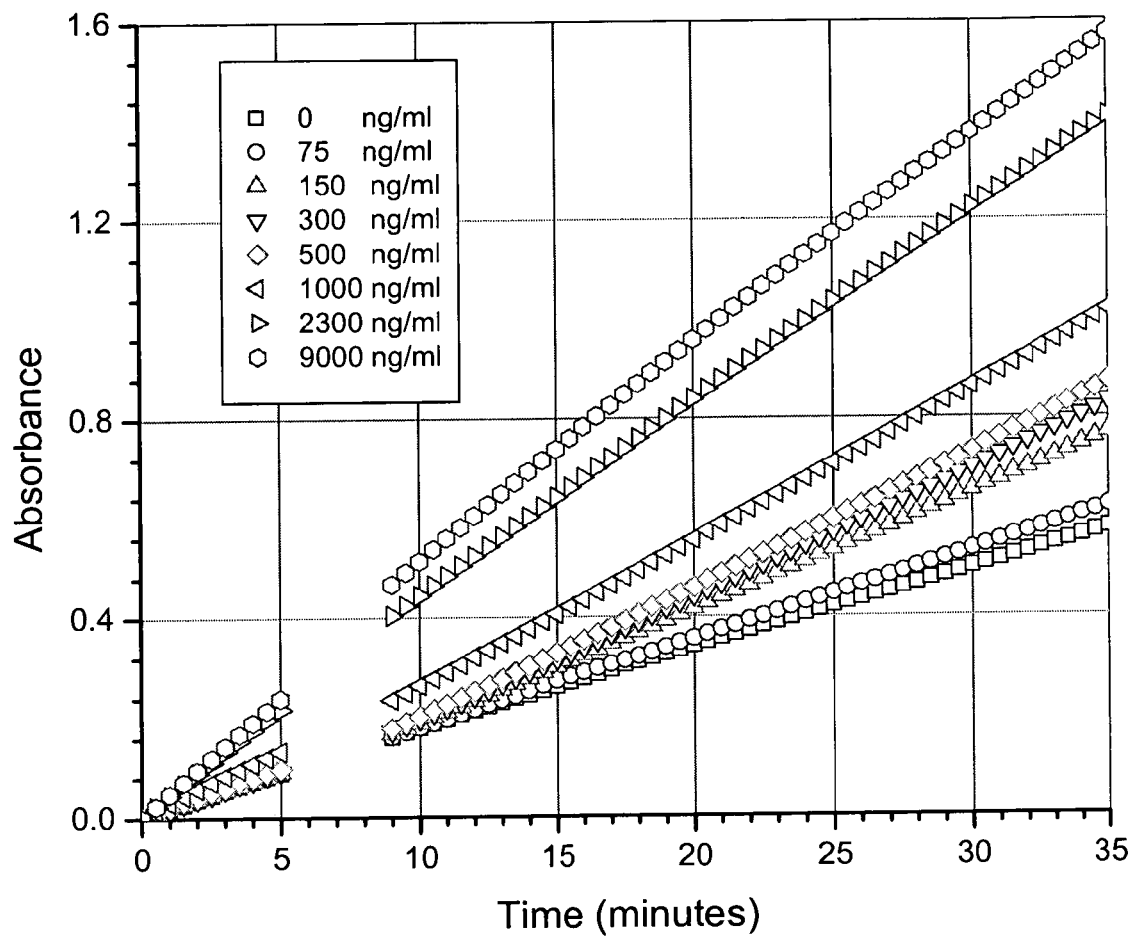
FIG. 7 is a set of curves presenting the absorbance a function of incubation time for composite assay.
Figure 8:
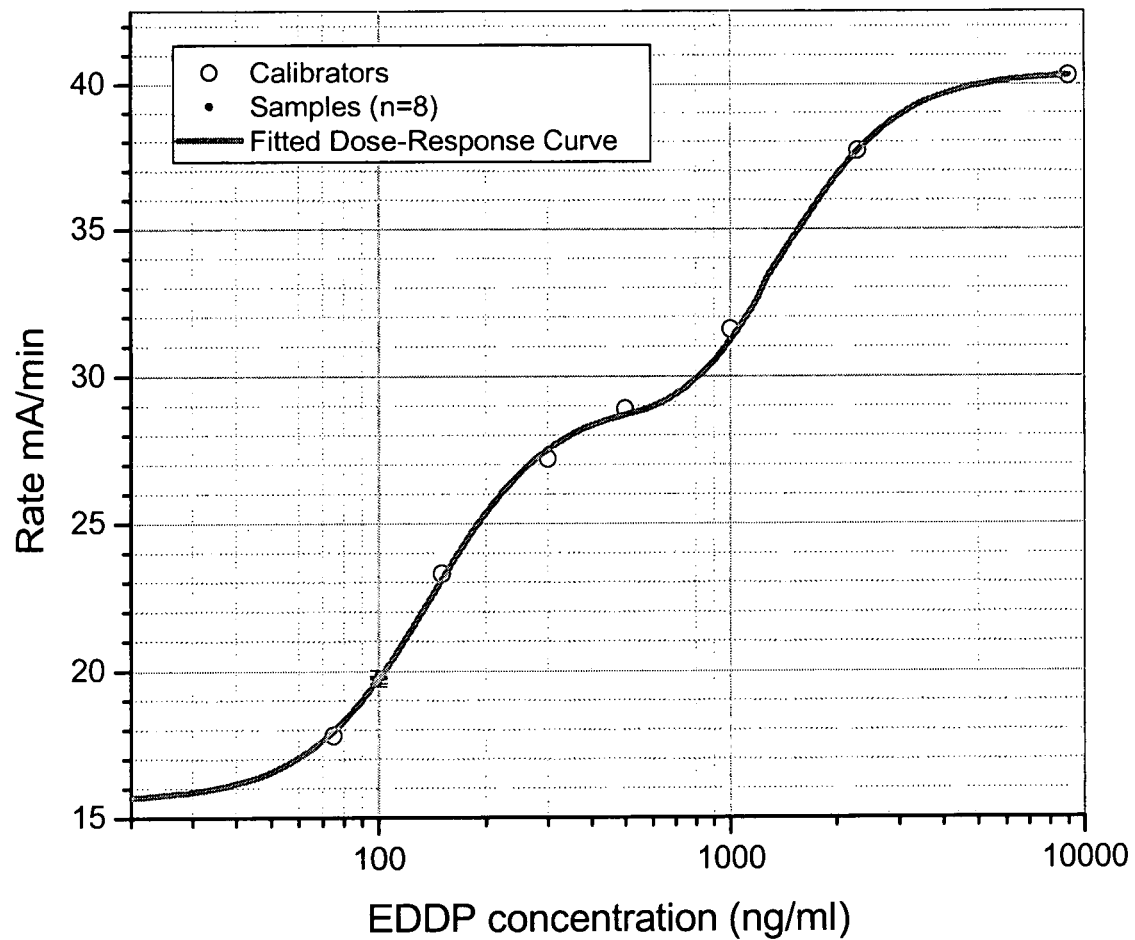
FIG. 8 represents the rate of change of absorbance after 30 minutes of incubation for the curves in FIG. 5. The sum of two logistic curves, which is fitted to measured points, represents the dose-response curve.

The time-dependent absorbance of the eight samples is plotted in FIG. 7. Unlike the concentration curves of FIG. 5, in which only the curve for a concentration of 150 ng/ml was clearly separated from the other concentration curves, almost all curves in FIG. 7 show a distinct mutual separation. However, due to the two-step reverse dilution process, the absorbance values alone are not amenable to accurate interpretation. Instead, the rate of change of absorbance provides a clear and meaningful presentation of the measured data. The rate of change of absorbance (measured at 30 minutes) is presented in FIG. 8, which clearly shows the new dose-response curve of the assay. In particular, the detection window (following the same convention as in the prior art assay) is broadened from the prior art range of approximately 58-580 ng/ml to the wider range of 75-2250 ng/ml. The dynamic range of 30 is also dramatically increased by a factor of 3 over the prior art value.

Figure 9:
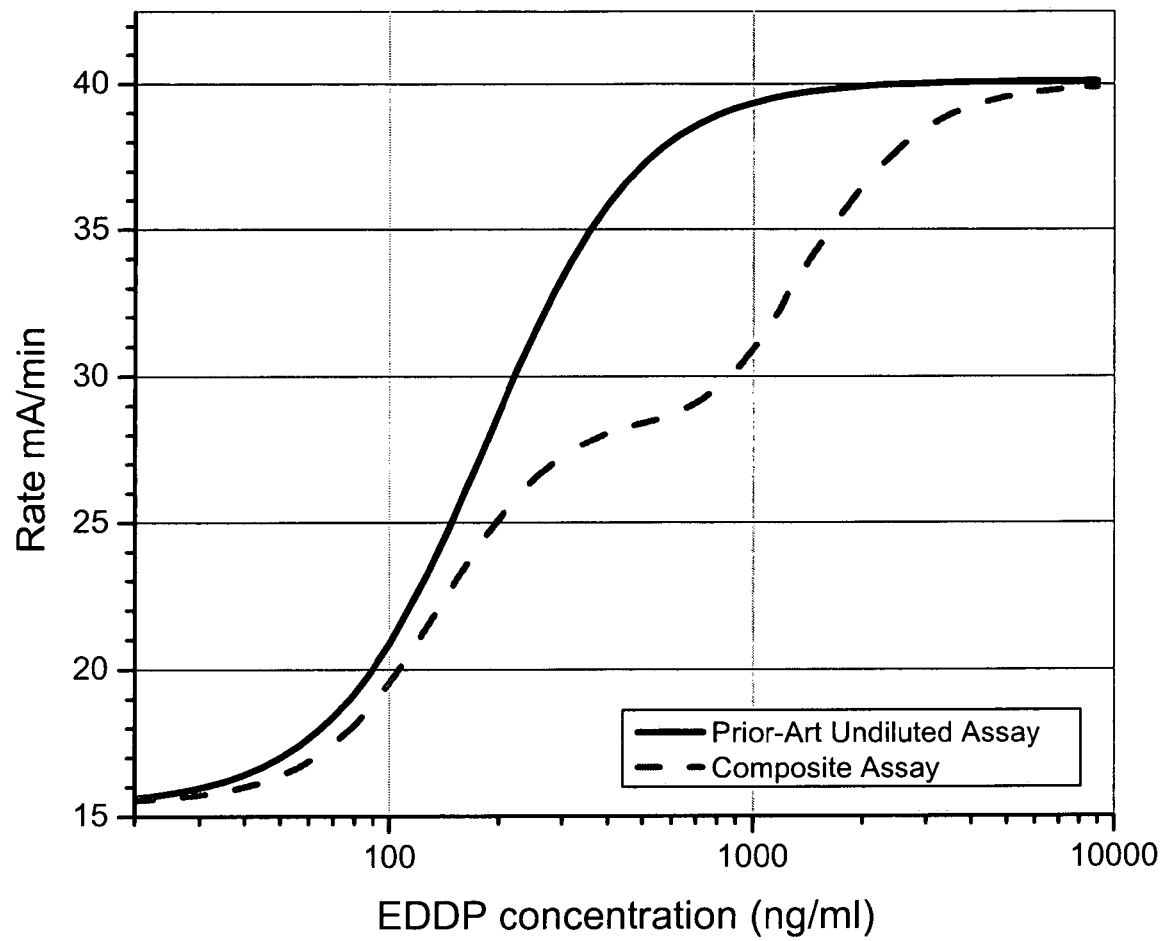
FIG. 9 compares the dose-response curves of assay performed in conventional and composite manners.

The new dose response curve, also shown with the prior art undiluted assay curve in FIG. 9, appears to be close to a numerical average of the prior art diluted and undiluted dose-response curves. Since the slope of the composite assay is everywhere less than maximum slope of the prior art assay, it can be understood that the enhanced dynamic range is obtained at the cost of a globally higher coefficient of variation for the composite assay. The new curve is accurately fit by the sum of two logistic curves. This accurate fitting with a simple and known function facilitates the recovery of unknown sample concentrations from a pre-determined calibration curve. In particular, the inversion can be achieved by the solution of a simple quadratic equation without requiring more elaborate numerical methods.

Figure 10:
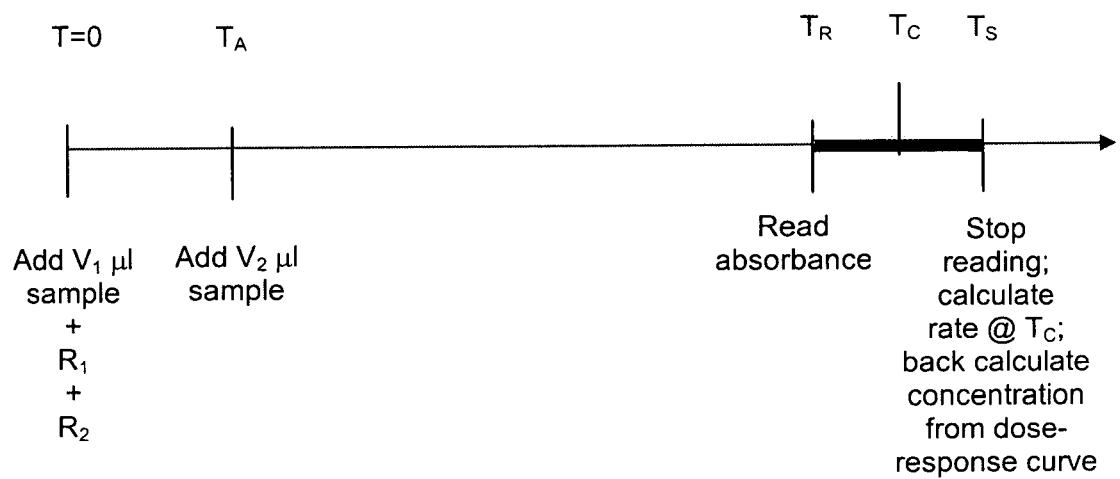
FIG. 10 schematically illustrates a timing protocol for the composite homogeneous immunoassay.

In the general context of homogeneous enzyme assays, the assay can be conducted following the following protocol, schematically illustrated in FIG. 10. At time T=0, the two reagents $R_1$ and $R_2$ are mixed with a volume $V_1$ of the sample. The mixture is then vortexed and incubated at a constant temperature for a time interval $T_a$. A volume $V_2$ of sample is then added and the mixture is again vortexed to insure sufficient mixing. The mixture is incubated until a time $T_R$, after which the absorbance is read until time $T_S$. The rate of change of absorbance at time $T_C$, where $T_C$ lies in the interval [$T_R$, $T_S$], is then calculated. The analyte concentration is calculated via a pre-determined dose-response curve.

Figure 2:
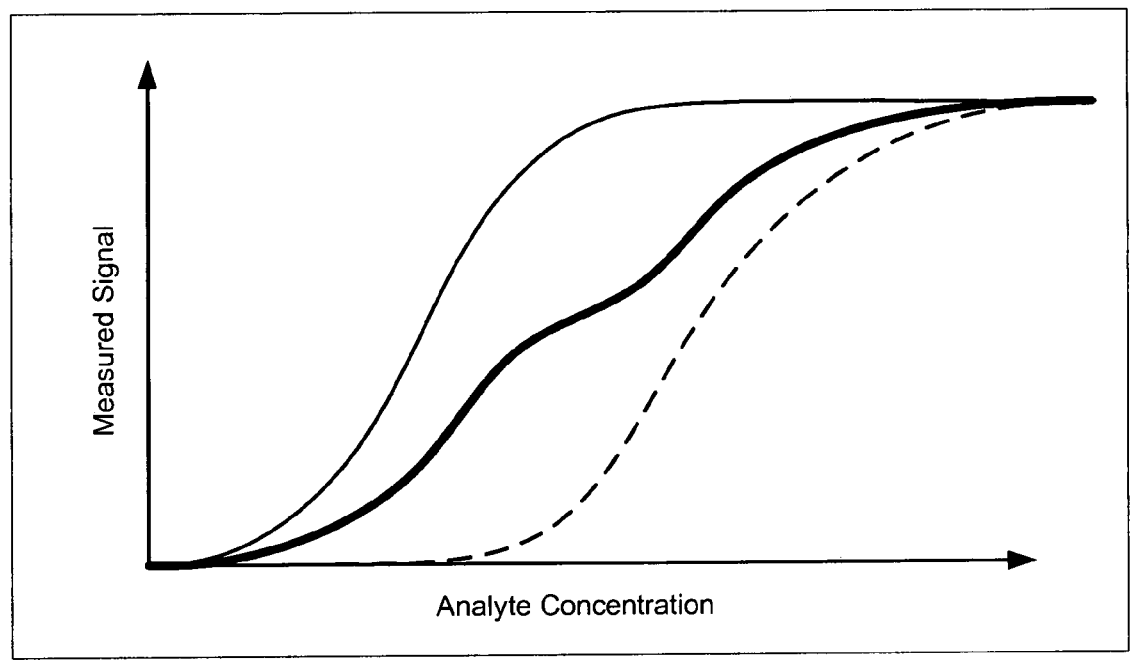
FIG. 2 is an illustration of an intermediate, non-equilibrium dose-response curve exhibited by the composite assay of the present invention.

In the specific case of dynamic rather than endpoint assays, such as in the example above for a homogeneous enzyme assay, another embodiment of the invention is possible that provides a more accurate measurement of the concentration of analyte over a specific range. This is achieved by making a measurement of the analyte concentration based on the signal obtained during or after the first incubation period, but prior to the addition of the second sample volume. The analyte concentration is obtained via a pre-determined dose-response curve using this method. Since the assay signal is characterized by a dose-response curve with a larger slope than that of the composite assay (as can be seen in FIG. 2), it provides a measurement with less error. However, this improved accuracy only occurs over a limited range of concentrations, and if the analyte concentration falls below this range then the second part of the composite assay can be performed to obtain an accurate measurement at a lower analyte concentration.

The precision and accuracy of the inventive composite assay for EDDP was also experimentally investigated. A calibration curve was initially obtained using the method described above and fitting the measured rate of change of absorbance to the sum of two logistic functions. A new set of eight composite assays were then performed, again using the above method, for identical samples with an EDDP concentration of 100 ng/ml. A quadratic solution of the calibration function was used to convert the measured rates of change of absorbance to inferred sample concentrations. The resulting sample concentrations are shown in Table 1 and also in FIG. 8. The results indicate that the exemplary assay can be performed with an accuracy of 2% and a precision of 1.5%.

TABLE 1

Inferred concentrations of EDDP in a set of 8 composite assays, in which the accurate concentration of EDDP is 100 ng/ml.

| True value | 100.0 | 100.0 | 100.0 | 100.0 | 100.0 | 100.0 | 100.0 | 100.0 |
|---|---|---|---|---|---|---|---|---|
| Measured value | 102 | 98 | 102 | 102 | 100 | 100 | 100 | 102 |

Although a preferred embodiment of the composite assay method employs sample dilution to achieve an accurate dilution factor for the first and second sample addition steps, the use of different sample volumes to obtain an effective dilution factor is also possible. For example, in the above description of the composite assay for EDDP, a sample volume of 2 µL was employed as the diluted sample. Later, a volume of 18 µL was chosen as the effectively undiluted sample. Although the analyte concentrations of both the 2 µL and the 18 µL volumes were identical, the net result of dispensing the 18 µL into the same reaction vessel as the 2 µL sample is reverse dilution with a factor of 10.

It is important to recognize that the dose-response curve obtained for the composite EDDP assay was a specific case of a general set of curves that can be tailored to suit the requirements of a particular assay. Indeed, the dose-response curve of the composite assay can be modified by varying the assay parameters. For example, the width of the detection window can be optimized by varying the dilution factor of the diluted and undiluted samples. Also, the shape of the curve is governed by the choice of the two incubation periods (i.e. the time period before the addition of the second sample volume, and the time period between adding the second sample volume and measuring the signal).

This control allows one to design an assay with a dose-response curve having a shape that is optimized for a given application. It can be observed in FIG. 8 that over the range of concentrations within the central zone of the detection window, the slope of the curve changes from a large slope to a smaller slope and then once again to a large slope. This occurs over the transition between the two linear ranges of the dose-response curve. The corresponding coefficient of variation of the assay will, in most cases, follow the same trend as this slope. In many diagnostic assays, it may not be desirable to have a coefficient of variation that worsens in the central zone of the detection window. Fortunately, the control over the dose-response curve provided by the assay parameters enables the creation of a single linear range within the central zone of the detection window. This is achieved by narrowing the dilution factor by an amount that sufficiently overlaps the two logistic functions that comprise the dose-response curve of the composite assay.

Figure 11:
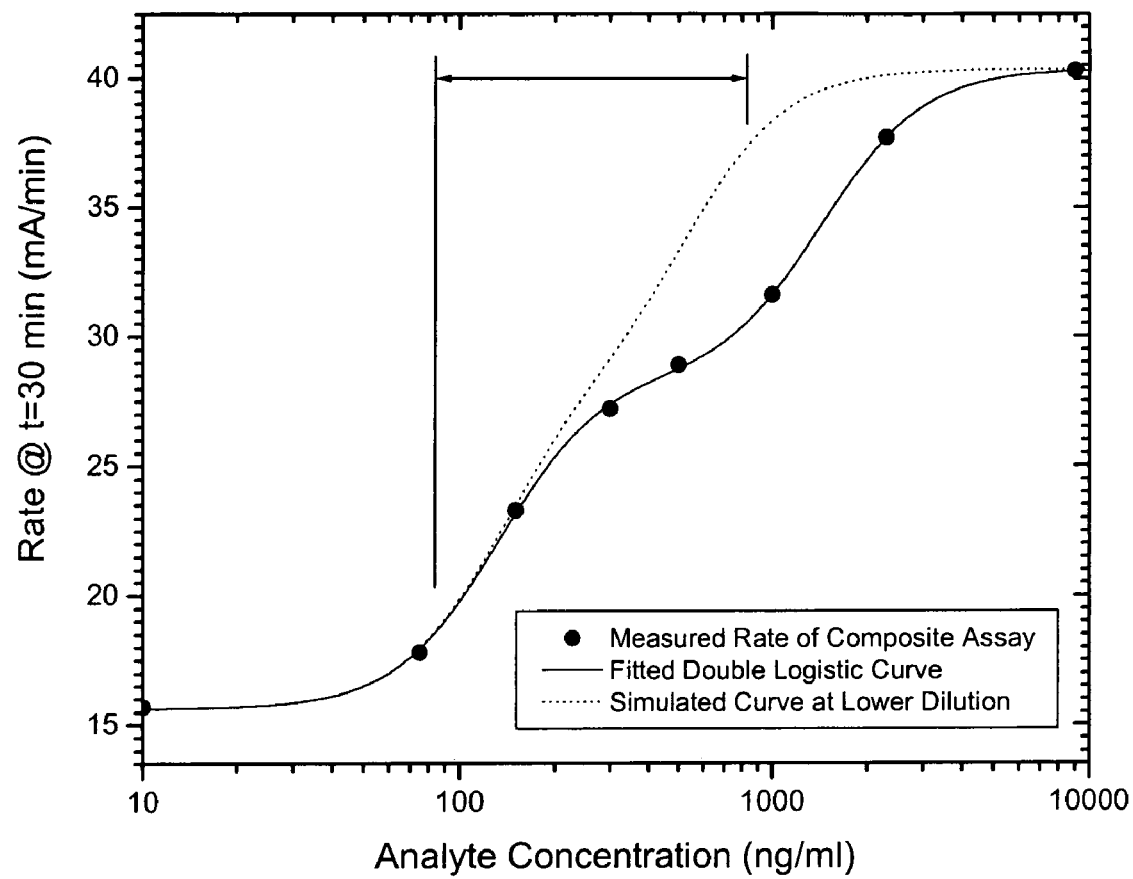
FIG. 11 plots the dose-response curve of the measured data for the EDDP composite assay with a simulated dose-response curve having a wider linear response range.

Such a scheme is illustrated in FIG. 11, in which a dose-response curve for a simulated EDDP composite assay with a smaller dilution factor is plotted with the measured dose-response curve of the composite EDDP assay described above. The simulation is achieved by changing the ratio of the parameters of the dual logistic function that dictate the dilution factor. The dual logistic function takes the general form:

$$y = a_0 + \frac{a_1}{\left(1 - \left(\frac{a_2}{x}\right)^{a_3}\right)} + \frac{a_4}{\left(1 - \left(\frac{a_5}{x}\right)^{a_6}\right)}, \quad (1)$$

where y is an assay signal, x is an analyte concentration, and $a_0$-$a_6$ are fitting parameters, and where the dilution factor is approximately equal to the ratio $a_2$-$a_5$. In the fitted dose-response curve shown in FIG. 8, this ratio is equal to 10.9, which is nearly equal to the dilution factor of 10 (the discrepancy may be explained by pipetting errors alone). The simulated curve in FIG. 11 can be obtained by changing the value of $a_2$ from 1150 ng/ml to 550 ng/ml, i.e. reducing the dilution factor to 5.2. This reduction of the dilution factor has the effect of producing a linear dose-response over a wide range of analyte concentrations as the upward curvature of the first logistic function is balanced by the downward curvature of the second logistic function. Although the dynamic range of this simulated dose-response curve is less than that of the measured composite assay, the simulated curve advantageously maintains a constant slope over an entire order of magnitude of analyte concentrations. In most cases, this behaviour will produce a constant coefficient of variation, which is a desirable characteristic of a diagnostic assay.

It is also possible that an assay may be preferably conducted with two separate linear ranges, i.e. for the determination of the presence of the analyte at a low-concentration cutoff and for the accurate quantification of the analyte concentration in a therapeutically relevant range of concentrations. Such a dose-response curve can be designed by controlling the dilution factor, as in the aforementioned example. If a large dilution factor (e.g. greater than 10) is chosen, the two logistic functions will be separated in the dose-response curve, producing two separate linear (and sensitive) windows of detection.

In another embodiment of the invention, the composite assay method can be modified to obtain optimal sensitivity over a broad detection window. A fixed volume of diluted sample is initially added. After the first incubation period, the signal (e.g. rate of change of absorbance for an enzymatic assay) is measured prior to the addition of the second (undiluted) variable sample volume. The measured signal is then used to obtain an estimate of the analyte concentration using a pre-determined calibration curve, exactly as in the prior-art assay method. However, the modified composite method proceeds by using the estimated analyte concentration to calculate the optimal dilution factor for a composite assay with maximal sensitivity.

If direct sample dilution can be employed to obtain the appropriate sample dilution factor, then a second sample with the appropriate dilution factor is used. Alternatively, if sample volume is used in place of sample dilution, the dilution factor is used to calculate the second sample volume. For example, if the estimated analyte concentration is ten times lower than the point of maximum slope of the diluted dose-response curve, then a dilution factor of ten is chosen. Accordingly, if sample volume is obtained to achieve reverse dilution, then ten times more sample is added in the second step. This choice places the point of maximum slope of the low-concentration logistic curve (produced by the undiluted sample) at the estimated sample concentration. In order to generate a suitable calibration curve for this assay method, a dose-response curve is generated at an intermediate dilution factor. Although this curve will only be valid for one specific dilution factor, it can be modified to fit with any dilution factor by changing the value of $a_5$ in equation 1. Specifically, $a_5$ can be replaced by the value given by dividing $a_2$ by the optimal dilution curve. This change modifies the shape of the dose-response curve that had been obtained with a specific dilution factor in such a way that the required dose-response curve for the optimal dilution factor is obtained.

Although the invention has been described in the context of a two-step composite assay, it is possible to generalize the method to a multi-step process in which multiple windows of detection are obtained. For example, it is possible to add a third reverse dilution step, in which more analyte is added than in the first and second sample addition steps. This third addition step can be employed to add a third detection window, widen the linear range of one of the first two detection windows, or widen a single broad linear dose-response curve.

In a final embodiment of the invention, a single one-step assay method is employed to obtain an improved dynamic range. The inventive assay method applies to any assay for which the dose-response curve is fitted by an S-shaped function, such as a logistic function. The present inventive assay is arrived at by modifying a known assay in such a way that a quantity of pure target analyte is added to one of the assay reagents or to the sample itself. In a preferred embodiment, the pure analyte is added to an assay reagent to which the analyte does not bind or react. The addition of analyte modifies the dose-response curve, compressing the range of signals observed. For example, in the case of a logistic curve is given by the functional form $$y = a_0 + \frac{a_1}{\left(1 - \left(\frac{a_2}{x}\right)^{a_3}\right)}, \quad (2)$$

where y is the assay signal, x is the analyte concentration in the sample, and $a_0$-$a_3$ are fitting parameters, the addition of sample corresponding to an analyte concentration of x' causes the dose-response curve to take the new form $$y = a_0 + \frac{a_1}{\left(1 - \left(\frac{a_2}{x+x'}\right)^{a_3}\right)}. \quad (3)$$

Figure 12:
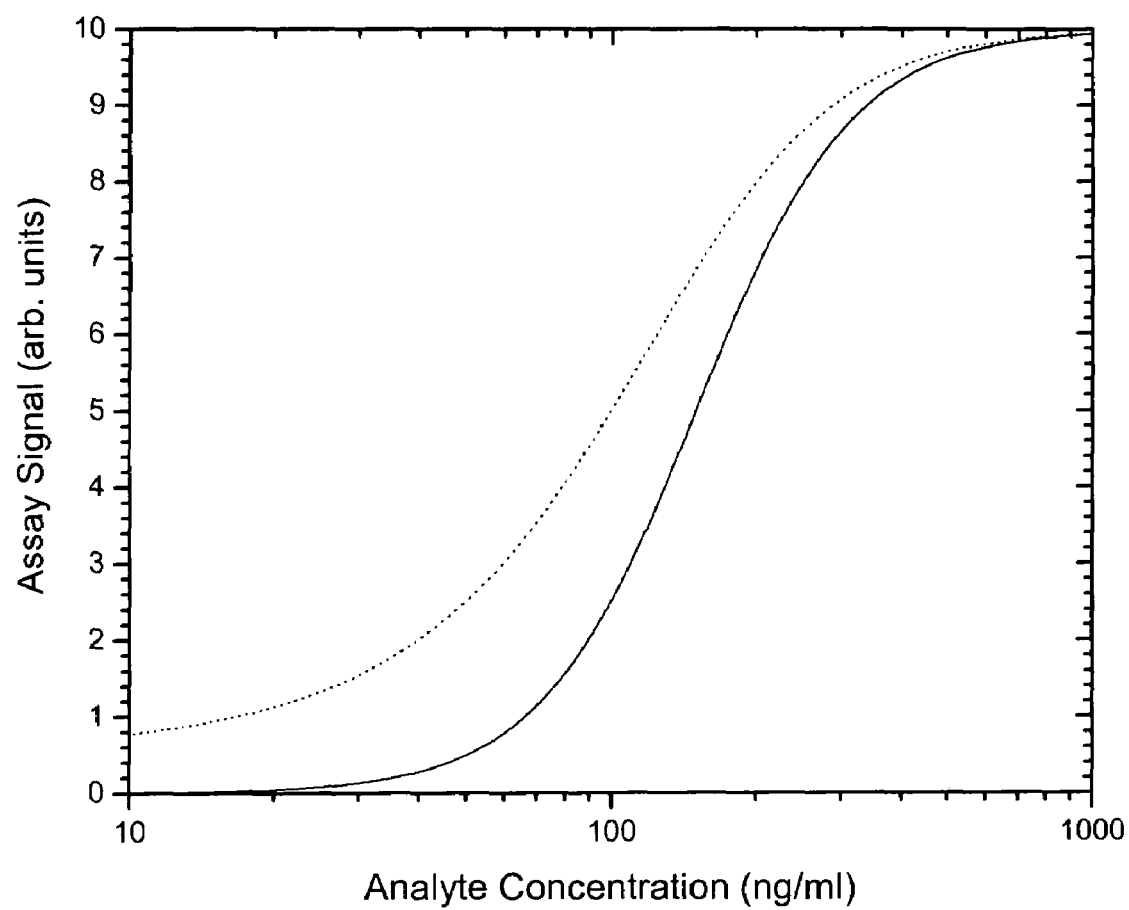
FIG. 12 plots dose-response curves of a fictitious assay exhibiting a logistic functional form. The dotted and solid lines show the response with and without the additional of pure analyte to one of the reagents, respectively.

The effect of the new functional form for a fictitious assay with logistical dose-response curve is shown in FIG. 12, where the dose-response curves are shown for the parameters $a_0$=0, $a_1$=10, $a_2$=150, and $a_3$=2.71, with and without an addition of sample corresponding to a concentration of 50 ng/ml.

Inspection of FIG. 12 clearly illustrates how the addition of pure sample broadens the dose-response curve and increases the slope of the dose-response curve at low analyte concentrations. This increase in slope translates directly to an increase in assay accuracy at lower analyte concentrations and thus a broader dynamic range.

Figure 13:
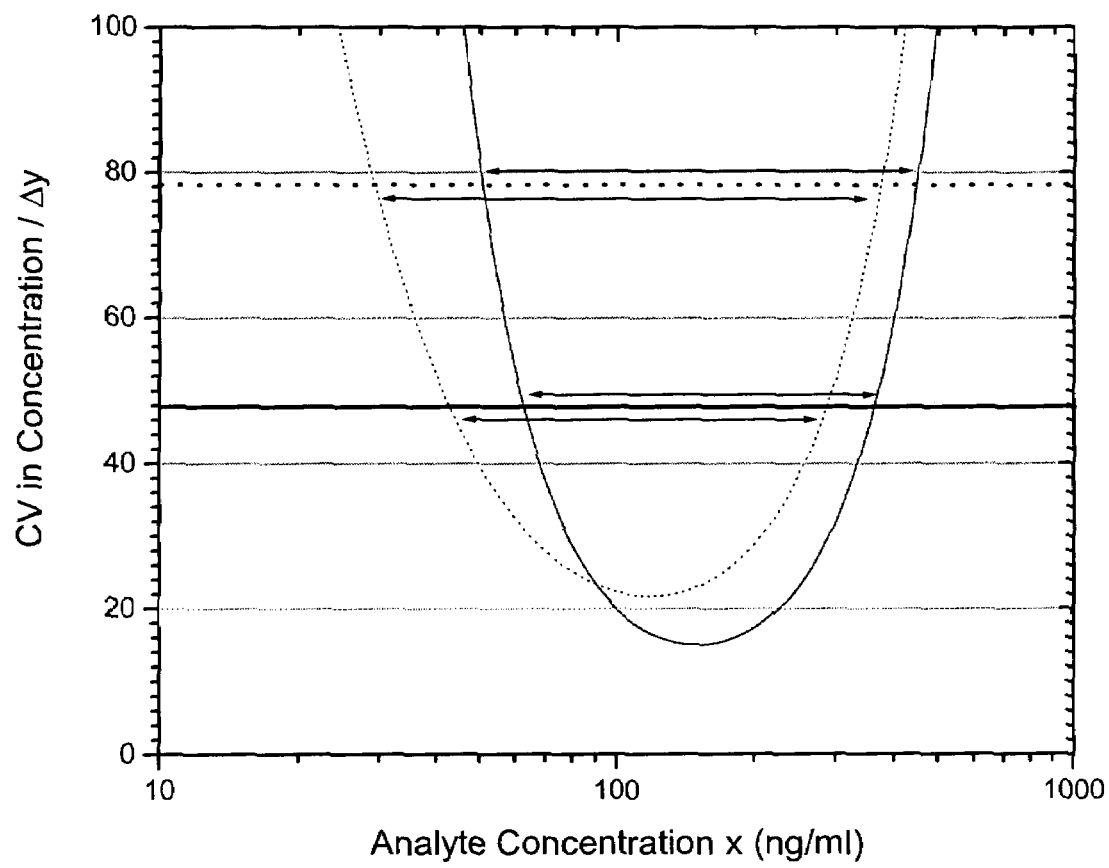
FIG. 13 plots the coefficient of variation divided by the assay signal error for a fictitious assay exhibiting a logistic functional form. The dotted and solid lines show the result with and without the additional of pure analyte to one of the reagents, respectively.

The actual increase in accuracy can be quantitatively examined by calculating the CV of both assays. The CV of an assay with a dose-response curve given by y=y(x) is equal to $$CV(\%) = 100 \Delta y \left[ \frac{dy}{d(\ln x)} \right]^{-1}, \quad (4)$$

where $\Delta y$ is the error in the assay signal y. In practice, the error $\Delta y$ can be assumed to be independent of analyte concentration. The CV, divided by a constant error $\Delta y$, is shown in FIG. 13 for both assays with and without sample addition. The solid curve shows the derivative of the assay signal without analyte addition and the dashed line shows the derivative of the assay with the addition of analyte.

Conventionally, the detection window is determined from the concentration range where the CV is less than or equal to its value measured at 10% and 90% of the maximum assay signal. This CV/$\Delta y$ value for the assay without sample addition is shown by the thick solid horizontal line in FIG. 13 (the CV/$\Delta y$ values at 10% and 90% of the maximum signal are equal for a logistic curve). As can be seen by the horizontal lines with arrowheads, the detection windows for both assays based on this definition are shifted, but nearly equal in span. If, however, the definition of the detection window is modified to signify the concentration range where the CV/$\Delta y$ is less than or equal to its value measured at 5% or 95% of the maximum signal, one obtains the thick dashed line for the CV/$\Delta y$ of the assay without sample addition. In this case, as shown again by the horizontal lines with arrowheads, the detection window of the assay with sample addition is significantly larger than that of the assay without sample addition.

The preceding discussion reveals how this embodiment of the invention can be employed to obtain an assay method with increased dynamic range. This increase in dynamic range, however, is accompanied by a decrease in assay accuracy over a wide concentration range within the detection window. This can be clearly seen in FIG. 13 by the smaller minimum CV/$\Delta y$ achieved by the assay with sample addition when compared to the assay without sample addition. In many applications, this decrease in accuracy will be acceptable if accompanied by an increase in dynamic range.

It is noted that those skilled in the art will readily appreciate that the aforementioned method of conducting a composite assay is not limited to homogeneous assays, but is generally applicable to all assay platforms involving competition between analyte in a sample and an analyte-conjugate. In particular, the term "competitive" assay is intended to include simultaneous competitive assays, inhibition assays, and also displacement assays.

As used herein, the terms "comprises", "comprising", "including" and "includes" are to be construed as being inclusive and open ended, and not exclusive. Specifically, when used in this specification including claims, the terms "comprises", "comprising", "including" and "includes" and variations thereof mean the specified features, steps or components are included. These terms are not to be interpreted to exclude the presence of other features, steps or components.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

Therefore what is claimed is:

1. A method of performing a competitive assay for a target analyte in a sample which may contain a concentration of the target analyte, comprising the steps of:
    a) combining in a vessel a first volume containing a first quantity of said sample and a first quantity of dilution buffer, a first reagent volume containing a known concentration of the target analyte conjugated to a an enzyme, and a second reagent volume containing one or more substrates upon which said enzyme acts and receptors having affinity for the target analyte, wherein said target analyte conjugated to said enzyme binds to said receptors;
    b) thermally incubating said vessel for a first time interval;
    c) adding a second volume containing a second quantity of said sample and a second quantity of dilution buffer to said vessel, whereby a ratio of an amount of said sample in said second volume to the amount of said sample in said first volume is equal to a prescribed dilution factor;
    d) thermally incubating said vessel for a second time interval, during which time an assay signal generated by the action of said enzyme on said one or more substrates is measured and a rate of change of said assay signal is determined, wherein the binding of said target analyte conjugated to said enzyme with said receptors decreases said assay signal, and wherein said signal is measured prior to achieving chemical equilibrium; and
    e) relating said rate of change of said assay signal to a concentration of said target analyte in said sample using a pre-determined dose-response curve.

2. The method according to claim 1 wherein said second quantity of dilution buffer is zero.

3. The method according to claim 1 wherein said first and second quantities of dilution buffer are zero and a difference between said first and second quantities of sample is employed to obtain said prescribed dilution factor.

4. The method according to claim 1 wherein the assay is a homogeneous assay.

5. The method according to claim 1 wherein said first volume and said first reagent volume are added to said vessel prior to the addition of said second reagent volume.

6. The method according to claim 1 wherein said first volume and said second reagent volume are added to said vessel prior to the addition of said first reagent volume.

7. The method according to claim 1 wherein said first reagent volume and said second reagent volume are added to said vessel prior to the addition of said first volume.

8. The method according to claim 1 wherein said vessel is vortexed prior to said first thermal incubation time interval.

9. The method according to claim 1 wherein said vessel is vortexed prior to said second thermal incubation time interval.

10. The method according to claim 1 wherein the prescribed dilution factor is chosen to obtain a dose-response curve with a linear response over a wide range of target analyte concentrations.

11. The method according to claim 1 wherein the prescribed dilution factor is chosen to obtain a dose-response curve with two separated linear responses over two different ranges of target analyte concentrations.

12. The method according to claim 1 including measuring an initial assay signal during or after said first time interval and before step c), and relating said initial assay signal to a concentration of said target analyte in said sample using a pre-determined dose-response curve for said initial assay signal.

13. A method of performing a competitive assay for a target analyte in a sample which may contain a concentration of the target analyte, comprising the steps of:
   a) performing a first sample addition step including combining in a vessel a first volume containing a first quantity of said sample and a first quantity of dilution buffer, and a first reagent containing a known concentration of the target analyte conjugated to an enzyme, and a second reagent volume containing one or more substrates upon which said enzyme acts and receptors having affinity for the target analyte, wherein said target analyte conjugated to said enzyme binds to said receptors;
   b) thermally incubating said vessel for a first time interval;
   c) performing one or more additional sample addition and incubation steps including adding an additional volume containing an additional quantity of said sample and an additional quantity of dilution buffer to said vessel, whereby the ratio of an amount of said sample in said additional volume to the amount of said sample used in an immediately preceding sample addition step is equal to a prescribed dilution factor and thermally incubating said vessel for an additional time interval;
   d) performing a final sample addition step including adding a final volume containing a final quantity of said sample and a final quantity of dilution buffer to said vessel, whereby the ratio of an amount of said sample in said final volume to the amount of said sample used in an immediately preceding sample addition step is equal to a prescribed dilution factor;
   e) thermally incubating said vessel for a final time interval, during which time an assay signal generated by the action of said enzyme on said one more substrates is measured and a rate of change of said assay signal is determined, wherein the binding of said target_analyte conjugated to said enzyme with said receptors decreases said assay signal, and wherein said signal is measured prior to achieving chemical equilibrium; and
   f) relating said rate of chance of said assay signal to a concentration of said target analyte in said sample using a pre-determined dose-response curve.

14. The method according to claim 13 wherein the assay is a homogeneous assay.

15. The method according to claim 13 wherein the first volume and said first reagent volume are added to said vessel prior to the addition of said second reagent volume.

16. The method according to claim 13 wherein the first volume and said second reagent volume are added to said vessel prior to the addition of said first reagent volume.

17. The method according to claim 13 wherein said first reagent volume and said second reagent volume are added to said vessel prior to the addition of said first volume.

18. The method according to claim 13 wherein said vessel is vortexted prior to said first thermal incubation time interval.

19. The method according to claim 13 wherein said vessel is vortexted prior to said additional thermal incubation time interval and said final incubation time interval.

20. The method according to claim 13 wherein said vessel is vortexted prior to each of said additional thermal incubation time intervals and said final incubation time interval.

21. The method according to claim 13 wherein the addition of said sample to said dilution buffer is employed to dilute the sample and obtain said prescribed dilution factors.

22. The method according to claim 13 wherein a difference in volume between said first, additional and final volumes is employed to obtain said prescribed dilution factors.

23. The method according to claim 13 wherein the prescribed dilution factors are chosen to obtain a dose-response curve with a linear response over a wide range of target analyte concentrations.

24. The method according to claim 13 wherein the prescribed dilution factors are chosen to obtain a dose-response curve with three separated linear responses over three different ranges of target analyte concentrations.

25. The method according to claim 13 wherein the prescribed dilution factors are chosen to obtain a dose-response curve with multiple separated linear responses over multiple different ranges of target analyte concentrations.

26. The method according to claim 13 including measuring an initial assay signal during or after said first time interval and before step c), and relating said initial assay signal to a concentration of said target analyte in said sample using a pre-determined dose-response curve for said initial assay signal.

27. A method of performing a competitive assay for a target analyte in a sample which may contain a concentration of the target analyte, comprising the steps of:
   a) combining in a vessel a first volume containing a first quantity of said sample and a first quantity of dilution buffer, and a first reagent volume containing a known concentration of the target analyte conjugated to an enzyme, and a second reagent volume containing one or more substrates upon which said enzyme acts and receptors having affinity for the target analyte, wherein said target analyte conjugated to said enzyme binds to said receptors;
   b) thermally incubating said vessel for a first time interval, during which time a first assay signal generated by the action of said enzyme on said one more substrates is measured;
   c) estimating said concentration of the target analyte in said sample by relating said measured first assay signal to said concentration of said target analyte in said sample using a pre-determined dose-response curve corresponding to said first assay signal;
   d) calculating an optimal dilution factor by dividing a concentration at which said pre-determined dose-response curve has a maximal slope by said estimated concentration of said target analyte in said sample;
   e) adding a second volume containing a second quantity of said sample and a second quantity of dilution buffer to said vessel, whereby a ratio of an amount of said sample in said second volume to the amount of said sample in said first volume is equal to said optimal dilution factor;
   f) thermally incubating said vessel for a second time interval, during which time a second assay signal generated by the presence of said enzyme conjugated to said target analyte is measured and a rate of change of said second assay signal is determined, wherein the binding of said target analyte conjugated to said enzyme with said receptors decreases said assay signal, and wherein said signal is measured prior to achieving chemical equilibrium; and
   g) relating said rate of change of said second assay signal to said concentration of said target analyte in said sample using a dose-response curve corresponding to said second assay signal.

28. The method according to claim 27 wherein in the event that said estimated concentration of the target analyte obtained in step c) is either zero or indiscernible from zero as a result of a signal-to-noise ratio of said measurement, said optimal dilution factor is chosen to be equal to a fixed value.

29. The method according to claim 27 wherein the assay is a homogeneous assay.

30. The method according to claim 27 wherein said first volume and said first reagent volume are added to said vessel prior to the addition of said second reagent volume.

31. The method according to claim 27 wherein said first volume and said second reagent volume are added to said vessel prior to the addition of said first reagent volume.

32. The method according to claim 27 wherein said first reagent volume and said second reagent volume are added to said vessel prior to the addition of said first volume.

33. The method according to claim 27 wherein said vessel is vortexted prior to said first thermal incubation time interval.

34. The method according to claim 27 wherein said vessel is vortexted prior to said second thermal incubation time interval.

35. The method according to claim 27 wherein the addition of the sample to the dilution buffer is employed to dilute the sample and obtain said optimal dilution factor.

36. The method according to claim 27 wherein a difference in volume between said first and second volumes is employed to obtain said optimal dilution factor.

37. The method according to claim 27 wherein a predefined dose-response curve is obtained at a fixed dilution factor chosen to give a dynamic range that spans a specific range of target analyte concentrations where concentrations of the target analyte in unknown samples are expected to lie, whereby signals obtained from a set of known dose-responses are plotted against their concentration, and fitting said signals and concentrations to the mathematical function given by $$y = a_0 + \frac{a_1}{\left(1 - \left(\frac{a_2}{x}\right)^{a_3}\right)} + \frac{a_4}{\left(1 - \left(\frac{a_5}{x}\right)^{a_6}\right)}$$

where y is the assay signal, x is the analyte concentration, and $a_0$ $a_6$ are unknown fitting parameters, wherein said unknown fitting parameters are obtained by mathematically fitting said signals and concentrations to said mathematical function, wherein said dose-response curve is obtained from said predetermined dose-response curve by replacing said parameter $a_5$ by an expression $a_2/f$, where f is equal to said optimal dilution factor.

* * * * *